ID 1995).

(12) United States Patent
Gropper et al.

(10) Patent No.: US 7,756,724 B2
(45) Date of Patent: Jul. 13, 2010

(54) SYSTEM AND METHODS FOR REAL-TIME WORKLIST SERVICE

(75) Inventors: Adrian Gropper, Watertown, MA (US); Sean Doyle, Watertown, MA (US); Terry Rosenbaum, Okemos, MI (US); Hamid Tabatabaie, Newton, MA (US); Kang Wang, Acton, MA (US)

(73) Assignee: Merge Healthcare Incorporated, Hartland, WI (US)

( * ) Notice: Subject to any disclaimer, the term of this patent is extended or adjusted under 35 U.S.C. 154(b) by 1769 days.

(21) Appl. No.: 10/301,486

(22) Filed: Nov. 21, 2002

(65) Prior Publication Data
US 2003/0126148 A1 Jul. 3, 2003

Related U.S. Application Data

(60) Provisional application No. 60/332,155, filed on Nov. 21, 2001.

(51) Int. Cl.
G06Q 10/00 (2006.01)
G06Q 50/00 (2006.01)
A61B 5/00 (2006.01)
G06F 19/00 (2006.01)
G06Q 40/00 (2006.01)

(52) U.S. Cl. .................................. 705/2; 705/3; 705/4

(58) Field of Classification Search ...................... 705/2, 705/3, 4
See application file for complete search history.

(56) References Cited

U.S. PATENT DOCUMENTS

| | | | | |
|---|---|---|---|---|
| 4,648,067 A * | 3/1987 | Repass et al. | ................ | 715/205 |
| 4,648,071 A * | 3/1987 | Repass et al. | ................ | 715/205 |
| 4,768,099 A | 8/1988 | Mukai | ........................ | 358/257 |
| 4,817,050 A | 3/1989 | Komatsu et al. | ............. | 364/900 |
| 4,959,769 A | 9/1990 | Cooper et al. | ................ | 364/200 |
| 4,996,662 A | 2/1991 | Cooper et al. | ................ | 364/900 |
| 5,001,569 A | 3/1991 | Shigyo | ........................ | 358/296 |
| 5,029,016 A | 7/1991 | Hiyama et al. | ............... | 358/403 |
| 5,068,745 A | 11/1991 | Shimura | ...................... | 358/403 |

(Continued)

FOREIGN PATENT DOCUMENTS

EP        0 684 565 A1     11/1995

(Continued)

OTHER PUBLICATIONS

Berrut et al., "Indexing Medical Reports in a Multimedia Environment: the RIME experimental approach," *ACM*, 187-197 (1989).

(Continued)

*Primary Examiner*—Gerald J. O'Connor
*Assistant Examiner*—Amber L Altschul

(57) ABSTRACT

A system and methods for organizing, manipulating, and displaying worklists of patient studies for access by medical personnel is provided. The patient studies may include medical images and data relating to medical images. In some embodiments, the worklists are easily customizable, to permit a wide range of tasks to be handled in the worklist system. Updated worklist information may be pushed to the appropriate workstations or users in nearly real-time, as updates become available, reducing errors that may be caused by outdated information in worklists. In some embodiments, worklists contain overlapping information, which permits numerous users to see the information, even if it is not immediately relevant to their tasks. This increased scrutiny may help to reduce errors.

23 Claims, 11 Drawing Sheets

U.S. PATENT DOCUMENTS

| | | | |
|---|---|---|---|
| 5,097,418 A | 3/1992 | Nurse et al. | 364/419 |
| 5,146,552 A | 9/1992 | Cassorla et al. | 395/145 |
| 5,276,793 A | 1/1994 | Borgendale et al. | 395/148 |
| 5,319,543 A | 6/1994 | Wilhelm | 364/401 |
| 5,321,520 A | 6/1994 | Inga et al. | 358/403 |
| 5,345,551 A | 9/1994 | Shelley et al. | 395/157 |
| 5,384,643 A | 1/1995 | Inga et al. | 358/403 |
| 5,416,602 A | 5/1995 | Inga et al. | 358/403 |
| 5,432,871 A | 7/1995 | Novik | 382/232 |
| 5,440,678 A | 8/1995 | Eisen et al. | 395/154 |
| 5,493,658 A | 2/1996 | Chiang et al. | 395/375 |
| 5,535,322 A | 7/1996 | Hecht | 395/155 |
| 5,574,573 A | 11/1996 | Ray et al. | 358/452 |
| 5,579,519 A | 11/1996 | Pelletier | 395/705 |
| 5,636,631 A | 6/1997 | Waitz et al. | 128/660.01 |
| 5,680,129 A | 10/1997 | Weinberger et al. | 341/65 |
| 5,724,582 A | 3/1998 | Pelanek et al. | 395/620 |
| 5,734,915 A | 3/1998 | Roewer | 395/773 |
| 5,740,428 A | 4/1998 | Mortimore et al. | 395/615 |
| 5,745,392 A | 4/1998 | Ergas et al. | 364/715.02 |
| 5,823,948 A * | 10/1998 | Ross et al. | 600/300 |
| 5,832,476 A | 11/1998 | Tada et al. | 707/2 |
| 5,844,961 A | 12/1998 | McEvoy et al. | 378/98.8 |
| 5,845,303 A | 12/1998 | Templeman | 707/517 |
| 5,854,888 A | 12/1998 | Ishikawa et al. | 395/116 |
| 5,870,767 A * | 2/1999 | Kraft, IV | 715/205 |
| 5,893,916 A | 4/1999 | Dooley | 707/523 |
| 5,903,676 A | 5/1999 | Wu et al. | 382/244 |
| 5,905,991 A | 5/1999 | Reynolds | 707/501 |
| 5,920,877 A | 7/1999 | Kolster | 707/512 |
| 5,950,207 A | 9/1999 | Mortimore et al. | 707/104 |
| 5,970,499 A | 10/1999 | Smith et al. | 707/104 |
| 5,970,505 A | 10/1999 | Ebrahim | 707/501 |
| 5,991,728 A * | 11/1999 | DeBusk et al. | 705/2 |
| 5,995,976 A | 11/1999 | Walker et al. | 707/104 |
| 6,006,236 A | 12/1999 | Young | 707/103 |
| 6,029,167 A * | 2/2000 | Evans | 707/4 |
| 6,047,259 A * | 4/2000 | Campbell et al. | 705/3 |
| 6,064,771 A | 5/2000 | Migdal et al. | 382/232 |
| 6,067,075 A | 5/2000 | Pelanek | 345/158 |
| 6,067,524 A * | 5/2000 | Byerly et al. | 705/3 |
| 6,067,542 A | 5/2000 | Cariño, Jr. | 707/4 |
| 6,073,109 A | 6/2000 | Flores et al. | 705/8 |
| 6,076,166 A | 6/2000 | Moshfeghi et al. | 713/201 |
| 6,101,407 A | 8/2000 | Groezinger | 600/407 |
| 6,115,640 A | 9/2000 | Tarumi | 700/99 |
| 6,117,079 A | 9/2000 | Brackett et al. | 600/437 |
| 6,122,403 A | 9/2000 | Rhoads | 382/233 |
| 6,151,581 A * | 11/2000 | Kraftson et al. | 705/3 |
| 6,199,071 B1 | 3/2001 | Nielsen | 707/204 |
| 6,208,974 B1 * | 3/2001 | Campbell et al. | 705/3 |
| 6,246,404 B1 | 6/2001 | Feigner et al. | 345/338 |
| 6,253,210 B1 | 6/2001 | Smith et al. | 707/104 |
| 6,260,021 B1 | 7/2001 | Wong et al. | 705/2 |
| 6,269,379 B1 | 7/2001 | Hiyama et al. | 707/104 |
| 6,272,470 B1 * | 8/2001 | Teshima | 705/3 |
| 6,286,129 B1 | 9/2001 | Agarwal et al. | 717/1 |
| 6,287,257 B1 | 9/2001 | Matichuk | 600/437 |
| 6,295,542 B1 | 9/2001 | Corbin | 707/501.1 |
| 6,311,192 B1 | 10/2001 | Rosenthal et al. | 707/200 |
| 6,314,452 B1 | 11/2001 | Dekel et al. | 709/203 |
| 6,351,547 B1 | 2/2002 | Johnson et al. | 382/128 |
| 6,351,761 B1 | 2/2002 | Cantone et al. | 709/202 |
| 6,411,836 B1 | 6/2002 | Patel et al. | 600/407 |
| 6,430,601 B1 | 8/2002 | Eldridge et al. | 709/206 |
| 6,442,691 B1 | 8/2002 | Blandford | 713/178 |
| 2001/0047517 A1 | 11/2001 | Christopoulos et al. | 725/87 |
| 2001/0051881 A1 | 12/2001 | Filler | 705/3 |
| 2002/0019751 A1 | 2/2002 | Rothschild et al. | 705/3 |
| 2002/0033844 A1 | 3/2002 | Levy et al. | 345/744 |
| 2002/0052551 A1 | 5/2002 | Sinclair et al. | 600/476 |
| 2002/0085026 A1 | 7/2002 | Bocionek et al. | 345/738 |
| 2002/0087359 A1 | 7/2002 | Bocionek | 705/2 |
| 2002/0091765 A1 | 7/2002 | Bocionek | 709/203 |
| 2002/0116227 A1 | 8/2002 | Dick | 705/3 |
| 2002/0122057 A1 | 9/2002 | Maloney | 345/744 |
| 2002/0143862 A1 | 10/2002 | Peterson | 709/203 |

FOREIGN PATENT DOCUMENTS

EP  0 684 566 A1  11/1995

OTHER PUBLICATIONS

Carr et al., "Link Services or Link Agents?," ACM, 113-122 (1998).
Neuwirth et al., "The Notes Program: A Hypertext Application for Writing from Source Texts," ACM, 11:121-141 (1987).
Quint et al., "Combining Hypertext and Structured Documents in Grif," ACM, 23-32 (1992).
Anonymous."Desert Radiologists Announces Plans to Launch eMed Wide Access(TM) Technology," DIALOG File 20, *Dialog Global Reporter*, No. 16477601 (May 2, 2001).
Tygar, "Atomicity in Electronic Commerce," ACM, 5:32-43 (1998).
PCT International Search Report for PCT/US02/13551 dated Nov. 8, 2002.
PCT International Search Report for PCT/US02/37442 dated Aug. 28, 2003.

* cited by examiner

| | | | Patient Name | Age/Sex | Patient ID | Time | Referring | Procedure | Prior | Images | Alert | Workflow |
|---|---|---|---|---|---|---|---|---|---|---|---|---|
| ▶ Thursday June 06 2002 | | | | | | | | | | | | |
| ▶ | ⊞ ⊕ ⊚ | | Martinez Peter | 54 M | 1231232 | 14:16 | Farr | Abd Angio | | 0 | | Ordered |
| | ⊞ ⊕ ⊚ | | Fern Margaret | 34 F | 3422341 | 14:15 | Baker | Head CT | | 0 | | Ordered |
| ▶ | ⊞ | | How Walter | 23 M | 4345232 | 13:56 | Farr | Head CT | | 0 | | Transferring |
| ▶ | ⊞ | | Thistle Patrick | 23 M | 4576933 | 13:34 | Abbot | Color US | 2 ▼ | 1 | | Transferring |
| | ⊞ | | | | | Thu 3/7/02 | 17:06 | Farr | Foot CR 3V | | 5 | | Imaged |
| | ⊞ | | | | | Fri 11/30/01 | 16:45 | Abbot | Head CT | | 7 | | Imaged |
| ▶ | ⊞ | | Crean Tom | 39 M | 9379762 | 13:12 | Baker | Color US | | 3 | | Imaged |
| ▶ | ⊞ | | Adams Ben | 24 M | 3342523 | 12:52 | Abbot | Head CT | | 2 | | Imaged |
| ▶ | ⊞ ⊕ ⊚ | | Wordie James | 49 M | 5782413 | 12:08 | Farr | Abd MR | | 4 | | Preliminary |
| ▶ | ⊞ ⊕ ⊚ | | Loman William | 78 M | 9038823 | 11:02 | Abbot | Shoulder CR | 2 ▲ | 2 | STAT | Preliminary |
| ▶ | ⊞ ⊕ ⊚ | | Vincent John | 54 M | 2346752 | 11:00 | Farr | Head MR | 1 ▲ | 3 | STAT | Final |
| ▶ | ⊞ ⊕ ⊚ | | Brown Olympia | 78 F | 2397423 | 10:44 | Abbot | Chest CR 2V | | 4 | | Final |
| ▶ | ⊞ ⊕ ⊚ | | Baker Alice | 29 F | 8347283 | 10:30 | Farr | Liver NM | | 5 | | Preliminary |
| ▶ | ⊞ ⊕ ⊚ | | Thom Tracy | 23 F | 2341234 | 11:00 | Farr | Head CT | 1 ▲ | 5 | STAT | Preliminary |
| ▶ | ⊞ ⊕ ⊚ | | Smith John | 78 M | 9089732 | 10:44 | Abbot | Head CT | | 3 | | |
| ▶ Wednesday June 05 2002 | | | | | | | | | | | | |
| ▲ 5 patients hidden | | | | | | | | | | | | |
| | ⊞ | | Wash Jennifer | 35 F | 2342333 | 17:34 | Abbot | Color US | | 5 | | Imaged |
| | ⊞ | | Corn Gabriel | 49 M | 3858232 | 16:14 | Farr | Foot CR 3V | | 7 | | Imaged |
| | ⊞ | | Hepsted Sally | 54 F | 4892934 | 16:09 | Abbot | Color US | | 5 | | Imaged |
| ▲ 23 patients hidden | | | | | | | | | | | | |
| ▶ Tuesday June 04 2002 | | | | | | | | | | | | |
| ▲ 42 patients hidden | | | | | | | | | | | | |

FIG. 5

| Patient Name | Age/Sex | Patient ID | Time | Referring | Procedure | Prior | Images | Alert | Workflow |
|---|---|---|---|---|---|---|---|---|---|
| Martinez Peter | 54 M | 1231232 | 14:16 | Farr | Abd Anglio | | 0 | | Ordered |
| Fern Margaret | 34 F | 3422341 | 14:15 | Baker | Head CT | | 0 | | Ordered |
| How Walter | 23 M | 4345232 | 13:56 | Farr | Head CT | | 0 | | Transferring |
| Thistle Patrick | 23 M | 4576933 | 13:34 | Abbot | Color US | 2 ▼ | 1 | | Transferring |
| | | Thu 3/7/02 | 17:06 | Farr | Foot CR 3V | | 5 | | Imaged |
| | | Fri 11/30/02 | 16:45 | Abbot | Head CT | | 7 | | Imaged |
| Crean Tom | 39 M | 9379762 | 13:12 | Baker | Color US | | 3 | | Imaged |
| Adams Ben | 24 M | 3342523 | 12:52 | Abbot | Head CT | | 2 | | Imaged |
| Wordie James | 49 M | 5782413 | 12:08 | Farr | Abd MR | | 4 | | Preliminary |
| Loman William | 78 M | 9038823 | 11:02 | Abbot | Shoulder CR | 2 ▲ | 2 | STAT | Preliminary |
| Vincent John | 54 M | 2346752 | 11:00 | Farr | Head MR | 1 ▲ | 3 | | Final |
| Brown Olympia | 78 F | 2397423 | 10:44 | Abbot | Chest CR 2V | | 3 | STAT | Final |
| Baker Alice | 29 F | 8347283 | 10:30 | Farr | Liver NM | | 4 | | Final |
| Thom Tracy | 23 F | 2341234 | 11:00 | Farr | Head CT | 1 ▲ | 5 | | Preliminary |
| Smith John | 78 M | 9089792 | 10:44 | Abbot | Head CT | | 3 | STAT | Preliminary |
| Wash Jennifer | 35 F | 2342333 | 17:34 | Abbot | Color US | | 5 | | Imaged |
| Com Babriel | 29 M | 3858232 | 16:14 | Farr | Foot CR 3V | | 7 | | Imaged |
| Hepsted Sally | 54 F | 4892934 | 16:09 | Abbot | Color US | | 5 | | Imaged |

| PATIENT DATA | 552 |
|---|---|
| STUDY DATA | 554 |
| INSTITUTION DATA | 556 |
| TIME DATA | 558 |
| ROLE DATA | 560 |

| NAME | 601 |
|---|---|
| CHECK-IN CRITERIA | 602 |
| HIDE CRITERIA | 604 |
| CHECKOUT CRITERIA | 606 |
| DISPLAY | 608 |
| ACTIONS | 610 |

ER Worklist

View: Choose Worklist

Thursday December 05 2002

| Patient Name | Age/Sex | Patient ID | Referring | Modality | Procedure | Priors | Images | Alert | Workflow |
|---|---|---|---|---|---|---|---|---|---|
| APPLETON ERNEST | 39 M | 20113943 | MACKLIN DR | CR | Chest CR 2V | 0 | 0 | | Ordered |
| HOW WALTER | 79 M | 4012237 | ABBOT DR | CT | Head CT | 0 | 0 | | Ordered |
| WORDIE JAMES | 38 M | 11131065 | ABBOT DR | MR | Head MR | 0 | 0 | | Ordered |
| ANTHONY SUSAN | 72 F | 5552033 | MACKLIN DR | CT | Abd CT | 2 | 165 | | Unverified |
| PARSONS CLAUDIA | 37 F | 2910655 | MACKLIN DR | MR | Abd MR | 2 | 276 | | Unverified |
| RILEY SEAMUS | 56 M | 4331141 | DOE JOHN | CT | Abd/Pelvis CT | 2 | 96 | | Unverified |
| THORN TRACY | 35 F | 2341123 | BAKER DR | CR | Foot CR 3V | 2 | 3 | | Unread |
| VINCENT JOHN | 50 M | 4450192 | MACKLIN DR | NM | Liver NM | 2 | 2 | | Unread |

Wednesday December 04 2002
9 patients hidden

Tuesday December 03 2002
13 patients hidden

Radiologist Worklist

Thursday December 05 2002

| Patient Name | Patient ID | Age/Sex | Referring | Modality | Procedure | Priors | Images | Alert | Workflow |
|---|---|---|---|---|---|---|---|---|---|
| APPLETON ERNEST | 20113943 | 39 M | MACKLIN DR | CR | Chest CR 2V | 0 | 0 | | Ordered |
| HOW WALTER | 4012237 | 79 M | ABBOT DR | CT | Head CT | 0 | 0 | | Ordered |
| WORDIE JAMES | 11131065 | 38 M | ABBOT DR | MR | Head MR | 0 | 0 | | Ordered |
| ANTHONY SUSAN | 5562033 | 72 F | MACKLIN DR | CT | Abd CT | 2 | 165 | | Unverified |
| PARSONS CLAUDIA | 2910655 | 37 F | MACKLIN DR | MR | Abd MR | 2 | 276 | | Unverified |
| RILEY SEAMUS | 4331141 | 56 M | DOE JOHN | CT | Abd/PeMs CT | 2 | 96 | | Unverified |
| THORN TRACY | 2341123 | 35 F | BAKER DR | CR | Foot CR 3V | 2 | 3 | | Unread |
| VINCENT JOHN | 4450192 | 50 M | MACKLIN DR | NM | Liver NM | 2 | 2 | | Unread |

Thursday December 04 2002

| Patient Name | Patient ID | Age/Sex | Referring | Modality | Procedure | Priors | Images | Alert | Workflow |
|---|---|---|---|---|---|---|---|---|---|
| BAKER ALICE | 5562023 | 72 F | MACKLIN DR | CT | Abd CT | 2 | 165 | | Unread |
| GRIMKE ANGELINA | 7182331 | 1 F | DOE JOHN | CR | Pediatric CR | 2 | 1 | | Unread |
| HOWARD HILTON | 8499028 | 54 M | BAKER DR | CT | Chest CT | 2 | 381 | | Preliminary |
| KEANE ROY | 60119939 | 39 M | MACKLIN DR | CR | Chest CR 2V | 2 | 2 | | Preliminary |
| LOMAN WILLIAM | 1923421 | 79 M | ABBOT DR | CT | Head CT | 2 | 167 | | Preliminary |
| MARTINEZ PETER | 9874532 | 55 M | FARR DR | DS | Abd Angio | 2 | 38 | | Preliminary |
| SALINAS ROBERTO | 6020164 | 55 M | DOE JOHN | CR | Neonatal Chest | 2 | 1 | | Preliminary |
| LOPEZ ALBERT | 1131055 | 38 M | ABBOT DR | MR | Head MR | 2 | 239 | | Final |
| THISTLE PATRICK | 80245211 | 64 F | FARR DR | US | Color US | 2 | 7 | | Final |

FIG. 10C

Ref Physical Worklist

Thursday December 05 2002

| Patient Name | Patient ID | Age/Sex | Referring | Modality | Procedure | Priors | Alert | Last Action | Workflow |
|---|---|---|---|---|---|---|---|---|---|
| LOMAN WILLIAM | 1923421 | 79 M | ABBOT DR | CT | Head CT | 2 | | Sun 17/11/2... | Preliminary |
| CLARK ROBERT | 1923421 | 79 M | ABBOT DR | CT | Head CT | 2 | | Sun 17/11/2... | Final |
| LOPEZ ALBERT | 11131055 | 38 M | ABBOT DR | MR | Head MR | 2 | | Sun 17/11/2... | Final |
| THORN TRACY | 23411123 | 35 F | BAKER DR | CR | Foot CR 3V | 2 | | Sun 17/11/2... | Unread |
| HOWARD HILTON | 8493028 | 54 M | BAKER DR | CT | Chest CT | 2 | | Sun 17/11/2... | Preliminary |
| BLACKBOROW PL... | 8493028 | 54 M | BAKER DR | CT | Chest CT | 2 | | Sun 17/11/2... | Final |
| COUZINS PHOEBE | 23411133 | 35 F | BAKER DR | CR | Foot CR 3V | 2 | | Sun 17/11/2... | Final |

940

SYSTEM AND METHODS FOR REAL-TIME WORKLIST SERVICE

CROSS-REFERENCE TO RELATED APPLICATIONS

This application claims the benefit of and priority to the co-pending U.S. Provisional Application Ser. No. 60/332,155, filed Nov. 21, 2001, entitled "Method and System for Real-Time Worklist Service," the entirety of which is incorporated herein by reference.

TECHNICAL FIELD

The invention relates generally to data management systems and more particularly to medical data management. More specifically, in one embodiment, the invention relates to systems and methods for organizing, manipulating, and displaying worklists of patient studies (including image files) for access by medical personnel.

BACKGROUND

Medical data management systems organize and manipulate a variety of data, including patient data, information on procedures and studies that have been scheduled for patients, reports and notes from doctors and technologists relating to procedures and studies, medical images, lab results, billing and insurance information, and many other types of information relevant to medical professionals and management of medical facilities. Many types of medical information may be organized into a workflow, in which the necessary data is passed from one staff member, doctor, group, or department to the next, to assist in providing each staff member with the information that is needed to perform his or her job. Some systems have provided worklists, which provide each staff member, doctor, group, or department with a list of tasks that are to be completed, along with information about each task.

Unfortunately, these worklist displays are often limited in scope, providing information relating only to one activity or set of activities, such as appointment schedules, or scheduled use of an ultrasound system. Such limited-scope systems seldom support tracking tasks from their inception to their completion, through numerous phases, staff members, and departments.

Because they tend to designed to perform a single task, most worklist systems for use in a medical environment are difficult to customize. In many cases, customization requires extensive software work, which may need to be performed by the manufacturer of the system with which the worklists will be used, or by specialized consultants.

Additionally, known worklist systems are often tightly focussed, so that they provide only the information that is immediately relevant to each user of the system. While this arrangement may help with efficiency, it provides little opportunity for information in the worklists to be seen by multiple users.

Another difficulty with worklist systems used in a medical environment is that the information in the worklist may quickly become outdated or stale as conditions change. In some medical environments, conditions may change more rapidly than the worklists are updated, leading to the possibility of errors due to inaccurate or outdated information in the worklists.

Some worklist systems attempt to address this difficulty by querying the database that stores information on tasks to be performed at short, regular intervals (i.e., polling the database). Unfortunately, as the number of workstations and users accessing the worklists increases, the number of queries that must be processed, and the amount of communications or network traffic generated by all of these queries can overwhelm the databases and networks of a medical data management system. This may be especially problematic in systems that handle other tasks, such as medical imaging, that place high demands on networks and database systems.

SUMMARY OF THE INVENTION

The invention in one embodiment provides a system and methods for organizing, manipulating, and displaying worklists of patient studies for access by medical personnel, and addresses many of the difficulties encountered in previously known worklist systems. In some embodiments, the worklists are easily customizable, to permit a wide range of tasks to be handled in the worklist system. In some embodiments, updated worklist information is pushed to the appropriate workstations or users in substantially real-time, as updates become available, reducing errors caused by outdated information in worklists. In some embodiments, worklists contain overlapping information, which permits numerous users to see the information, even if it is not immediately relevant to their tasks. This increased multiple user scrutiny helps to reduce operator errors.

Broad-based use of real-time worklists according to the invention within a healthcare institution may enable that institution to significantly reduce the risk of clinician induced errors, and significantly increase the likelihood that any errors that do occur will be noticed and acted upon by other users of the real-time worklists. Additionally, because of the overlapping data contained in the sets of worklists used by various clinicians, the benefits derived from use of real-time worklists according to the invention may be effectively self-managing. The self-managing nature of the system may result from wide deployment of worklists, such that multiple clinicians note each step in the process, combined with real-time unprompted updates to each of the worklists.

In one aspect, the invention provides a method and system of providing worklist information to users of a medical data management system by providing numerous worklist items, each of which includes a set of data items. Worklists are assembled from the worklist items by using a customizable set of scoping rules to determine the worklist items to be included in each worklist. Each worklist is sent to appropriate client computers for display to a user almost immediately after the worklist is assembled, providing nearly real-time updates of the worklists. Such nearly real-time updates sent to a client computer, without the client computer requesting the item, is referred to herein as "pushing" worklists to the client computer.

In some embodiments, the customizable set of scoping rules is user customizable, while in some embodiments the scoping rules are customizable by a system administrator. In some embodiments, the data items include medical study data, patient data, patient location information, or institution data (such as the name of the medical institution, departmental information, the name of a treating physician, etc.).

In some embodiments, the method and system includes automated generation of a subset of the worklist items for inclusion in a worklist. Some embodiments include automated updating of a subset of the worklist items in response to an action being taken with respect to a data item in the set of data items. In some embodiments, the method and system includes automated adding or removal of worklist items in response to actions being taken with respect to a data item.

Some embodiments provide a graphical user interface for entering worklist items. In some embodiments the worklist items are provided by the system receiving orders for medical studies. These orders may be placed by a referring physician, and may request, for example, that medical images be taken.

Some embodiments use a messaging system to send the worklists to the client computers. In certain of these embodiments, the messaging system is compatible with a known messaging system standard, such as the Java™ Message Service (JMS). In some embodiments, the worklists are sent to the client computers as XML objects.

In some embodiments, assembling the worklists involves applying a set of check-in criteria associated with each worklist to determine which of the worklist items should be included in each worklist. The check-in criteria may include, for example, a list of modalities, a list of status fields, and/or other lists of criteria. Worklist items are included in the worklist if they have data values in the set of data items that match the lists of criteria. In some embodiments, the worklist items include a scheduled time, and the check-in criteria includes a time indicator, which specifies a time window. In one feature, worklist items having scheduled times within the time window are included in the worklist.

In some embodiments, a set of checkout criteria associated with each worklist are used to remove worklist items that match the checkout criteria from a worklist.

In some embodiments, each worklist is associated with one or more users, and sending worklists to the client computers involves determining which client computers should receive the worklists, based on the users with which each worklist is associated.

In some embodiments, the medical data management system manages a medical imaging system, and the set of data items includes a pointer to a medical image.

In another aspect, the invention provides a method and system for displaying a customizable worklist to a user of a medical data management system. This is done by receiving a worklist pushed from a real-time worklist service. The worklist may contain numerous worklist items, each of which may include numerous data items. Next, a set of the data items included in the worklist items are selected for display, based on a customizable set of display attributes associated with the worklist. The selected data items are then displayed for each of the worklist items that is displayed in the worklist. In some embodiments the worklists are displayed in a Web browser. In some embodiments, the worklist items that are displayed are sorted according to a sort order specified in the set of display attributes associated with the worklist.

In some embodiments, certain of the worklist items may be hidden. The set of worklist items that are to be hidden in the display is determined based on a set of "hide criteria" associated with the worklist. In certain such embodiments, information relating to the hidden items, such as the number and type of hidden items is displayed.

In some embodiments, a set of action icons are displayed with each of the worklist items. In certain such embodiments, the set of action icons displayed is determined by a list of actions associated with the worklist. In some embodiments, one of the action icons causes a medical image associated with a worklist item to be displayed.

In some embodiments, each user may have a set of preferences for viewing a particular worklist. These preferences affect which data items are displayed in the worklist, and may be specified by the user.

In another aspect, the invention provides a method and system for providing worklist information concurrently to numerous users of a medical data management system by defining scoping rules for items to be included in each of the worklists, wherein the scoping rules permit the same item to appear in more than one of the worklists. The scoping rules provide criteria are applied to a set of worklist items to populate the worklists in such a way that two or more of the worklists concurrently include the same item. The worklists are displayed on a client computer using a graphical user interface that may be organized in a consistent manner across the worklists. By including overlapping items in numerous worklists, the invention subjects the items to scrutiny by several different users, which helps to identify errors in the worklists and to reduce user errors related to attending to such overlapping items in the worklists In another aspect, the invention provides a method and system for reducing the occurrence of errors in information displayed in a worklist for a medical data management system by displaying substantially the same information and in two or more different worklists that are used by two or more groups of users. In some embodiments, the method further includes updating the information displayed in the two or more different worklists in substantially real-time as changes occur that affect the information in the worklists. In some embodiments, the worklists are displayed in a graphical user interface that is organized consistently across the worklists. In some embodiments, the worklists may be organized based on patient data, study data, institution data, time data, or role data. In some embodiments, the medical data management system includes a medical imaging system.

In a further aspect, the invention provides a medical data management system and methods that includes a worklist module that employs numerous worklist items, each of the worklist items including a set of data items. The worklist module assembles worklists from the worklist items by using a set of criteria to determine the worklist items that should be in each worklist. The system and methods use a real-time worklist service module to send the worklists to client computers that display the worklists by pushing (i.e. sending without a request) the worklists to the client computers.

In some embodiments, the medical data management system and methods include an image store that stores medical image data. The worklist items may contain pointers to medical image data in the image store.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments of the invention are described with reference to the following drawings, in which:

FIG. 3 shows an example of an order entry screen in accordance with an embodiment of the invention;

FIG. 4 shows an example of a worklist screen in accordance with an embodiment of the invention;

FIG. 5 shows an additional view of a worklist screen, highlighting action icons used in accordance with an embodiment of the invention;

FIG. 6 shows a block diagram of numerous types of data that may be displayed in worklists, and that may be used to organize worklists, in accordance with an illustrative embodiment of the invention;

FIG. 7 is a block diagram that shows the structure of a worklist record that may be used to define and customize a worklist, in accordance with an embodiment of the invention;

FIGS. 10A-10C show examples of several overlapping worklists, in accordance with an illustrative embodiment of the invention.

DESCRIPTION

The invention provides a system and methods for organizing, manipulating, and displaying worklists for use in a data management system. The system and methods are described illustratively as applying generally to a medical data management system, and more particularly to a medical data management system that handles patient studies that may contain medical image data. However, the worklist system and methods may be applied to other data management systems for use, for example, by a variety of medical professionals.

Broad-based use of real-time worklists according to the invention within a healthcare institution may enable that institution to significantly reduce the risk of clinician induced errors, and significantly increase the likelihood that any errors that do occur will be noticed and acted upon by other users of the real-time worklists. Additionally, because of the overlapping data contained in the sets of worklists used by various clinicians, the benefits derived from use of real-time worklists according to the invention may be effectively self-managing. The self-managing nature of the system may result from wide deployment of worklists, such that multiple clinicians note each step in the process, combined with real-time unprompted updates to each of the worklists.

Figure 1:
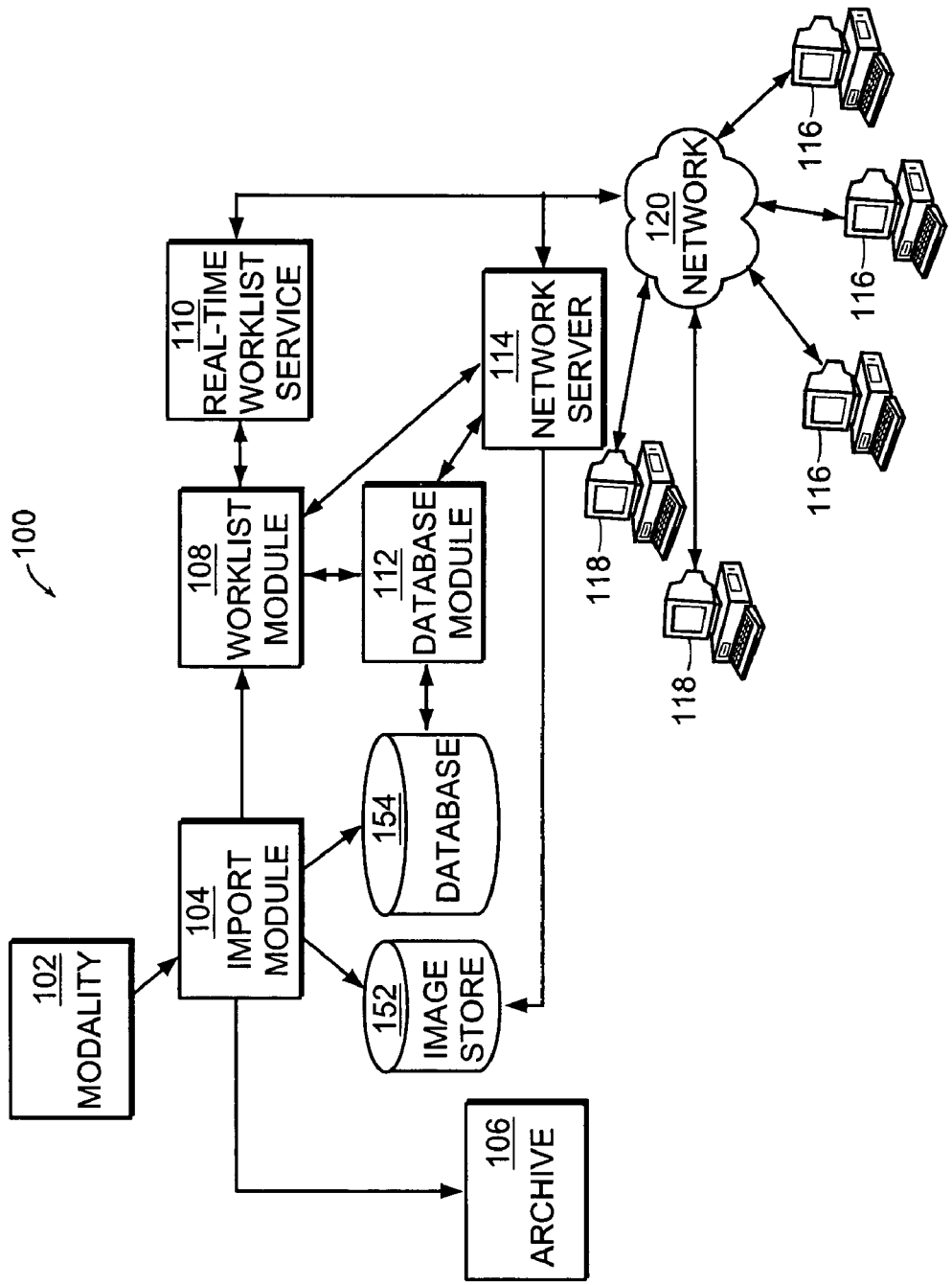
FIG. 1 is a block diagram of a medical data management system for use with an embodiment of the invention.

FIG. 1 is a conceptual block diagram depicting an overview of an exemplary medical data management system for use with an illustrative embodiment of the invention in which the patient studies that are handled by the system may contain medical image data. It should be understood that the system and methods of the invention may be used with other data management systems, including medical data management systems that do not involve medical image data. For example, the system and methods could be used in a medical data management system that tracks the status of patients within a hospital, or that tracks lab studies in a hospital environment. A similar medical data management system, suitable for use with the present invention, is described in commonly owned, co-pending U.S. patent application Ser. No. 10/135,879, filed Apr. 30, 2002, and entitled "System and Method for Repository Storage of Private Data on a Network for Direct Client Access," the entirety of which is incorporated herein by reference.

The illustrative medical data management system 100 includes at least one modality 102, which may be an imaging device, such as an X-ray system, a "Magnetic Resonance Imaging" (MRI) system, a film digitizer, or other radiological or medical imaging system or imaging device. The modality 102 typically generates images and header information in the "Digital Image Communications in Medicine" (DICOM) format, and sends such images to an import module 104.

The import module 104 receives the image and header information from the modality 102, and processes the received information to generate one or more images, which are stored in an image store 152, and a patient study descriptor, which is stored in a database 154. In some embodiments, the import module 104 may include an image coding function (not shown) that converts images into a standard format, such as the JPEG 2000 format, prior to storing the images in the image store 152. In some embodiments, the import module 104 may store images in the image store 152 in either a compressed format (in some illustrative embodiments, using lossy compression), an uncompressed format, or in both a lossy compressed format and an uncompressed format. Optionally, the import module 104 sends information, including the images, to an archive 106, which provides permanent storage for the images and other data. In some embodiments, the archive 106 is a commercially available medical image archive system, such as those available from Amicas, Inc., of Boston, Mass.

The import module 104 also transmits the patient study descriptor, including information such as patient name, age, sex, and time and date of a study to the database 154, using file identifiers that are transmitted to the import module 104 by the modality 102, or that are generated by the import module 104. In some illustrative embodiments, the file identifiers provide, for example, a descriptive name, a path to the file location and/or a random unique identifier (RUID). The patient study descriptor information contains links to the corresponding patient medical images that are stored in the image store 152. The patient study descriptor information may also be entered or updated by appropriate medical personnel via a network 120 using a workstation, such as a network workstation 116 or an imaging workstation 118.

The network workstations 116 are workstations that communicate with a network server 114 over a network 120, and that receive messages from the real-time worklist service 110 to display worklists, view images, enter orders, and to perform other activities using the system 100. In general, the network workstations 116 may be personal computers running a Web browser, such as Internet Explorer™, available from Microsoft Corporation, of Redmond, Wash. The network 120 may be any network, including a local area network, a private wide area network, the Internet, a wireless network, a combination of these (e.g., a wireless network that connects to the Internet, etc.), or any other communications network or combination of networks that is capable of transferring data.

The import module 104 also communicates with a worklist module 108, which prepares worklists for display on the network workstations 116 or the imaging workstations 118. The worklists contain information about patient studies that need attention from the medical personnel who use the network workstations 116 and the imaging workstations 118. For example, when an image is generated, the import module 104 sends a message to the worklist module 108, which places a worklist item, containing selected patient study information related to the image, as well as a link to the image into the worklist of an imaging technician who is responsible for verifying the image. According to the illustrative embodiment, once the technician verifies the image, the worklist module 108 removes the worklist item from the technician's worklist, and adds it to the worklist of a medical doctor, such as a radiologist, who will read the image. More complete information on the illustrative operation of the worklist module 108 and on worklists is provided below.

As will be described in greater detail below, the worklist module 108 uses a real-time worklist service 110 to cause the worklists displayed on the network workstations 116 and the imaging workstations 118 to be updated in substantially real-time as additional information and items become available for the worklists. In some embodiments, the real-time work-list service 110 "pushes" the appropriate worklist information to workstations that display worklists, through a network messaging system.

The worklist module 108 accesses data in the database 154 through a database module 112. The database module 112 provides an interface and services through which other parts of the system 100, including the network server 114 and worklist module 108 access patient study descriptor information and other information stored in the database 154.

According to the illustrative embodiment, the network server 114 provides Web-based access to worklists, patient study data, and images to users of the network workstations 116 and the imaging workstations 118. The network server 114 uses the HyperText Transfer Protocol (HTTP) to transfer information between the system 100 and the network workstations 116 and the imaging workstations 118. The network server 114 may be a standard Web server product, such as the Apache™ Web server, available from the Apache Software Foundation, or the Microsoft™ IIS Web Server, available from Microsoft Corporation, of Redmond, Wash. The network server 114 may execute on the same computer system as other portions of the system, or may execute on a separate computer or bank of computers.

Preferably, the Web browser used on the network workstations 116 is capable of running applets written in the Java™ programming language, or another client-side programming language that can be executed within a Web browser. According to the illustrative embodiment, client software for displaying worklists may be downloaded from the network server 114 for execution within the browser on a network workstation 116.

The imaging workstations 118 are similar to the network workstations 116, but include specialized display hardware for viewing high-resolution images and specialized software for diagnostically viewing images. In some illustrative embodiments, the imaging workstations 118 may use a Web browser to display worklists. However, in other illustrative embodiments, the imaging workstations 118 use proprietary client-side software to display worklists as part of the functionality of the specialized image viewing software.

In addition to the network workstations 116 and the imaging workstations 118, many different devices (not shown) may be used to display worklist information. For example, personal digital assistants and wireless devices may be employed to communicate across the network 120 to display worklists and images. In general, any device capable of executing a Web browser and communicating with the system 100 via the network 120 may display worklists in accordance with some embodiments of the invention. For devices capable of having messages pushed to them, nearly real-time updates of worklist information are available through the real-time worklist service 110. For devices that are not capable of receiving such messages, such as some wireless devices, the worklist information is made available or updated, for example, at a request from the user, or when the user device polls the system 100, preferably through the network server 114.

It should be understood that the system depicted in FIG. 1 is only one possible configuration for a medical information system with which an embodiment of the invention may be used. The various modules and components depicted in FIG. 1, such as the import module 104, the archive 106, the worklist module 108, the real-time worklist service 110, the database module 112, the network server 114, the image store 152, and the database 154 generally represent processes or logical operations. Two or more such modules or components may be present on the same computer, or on separate computers.

Figure 2:
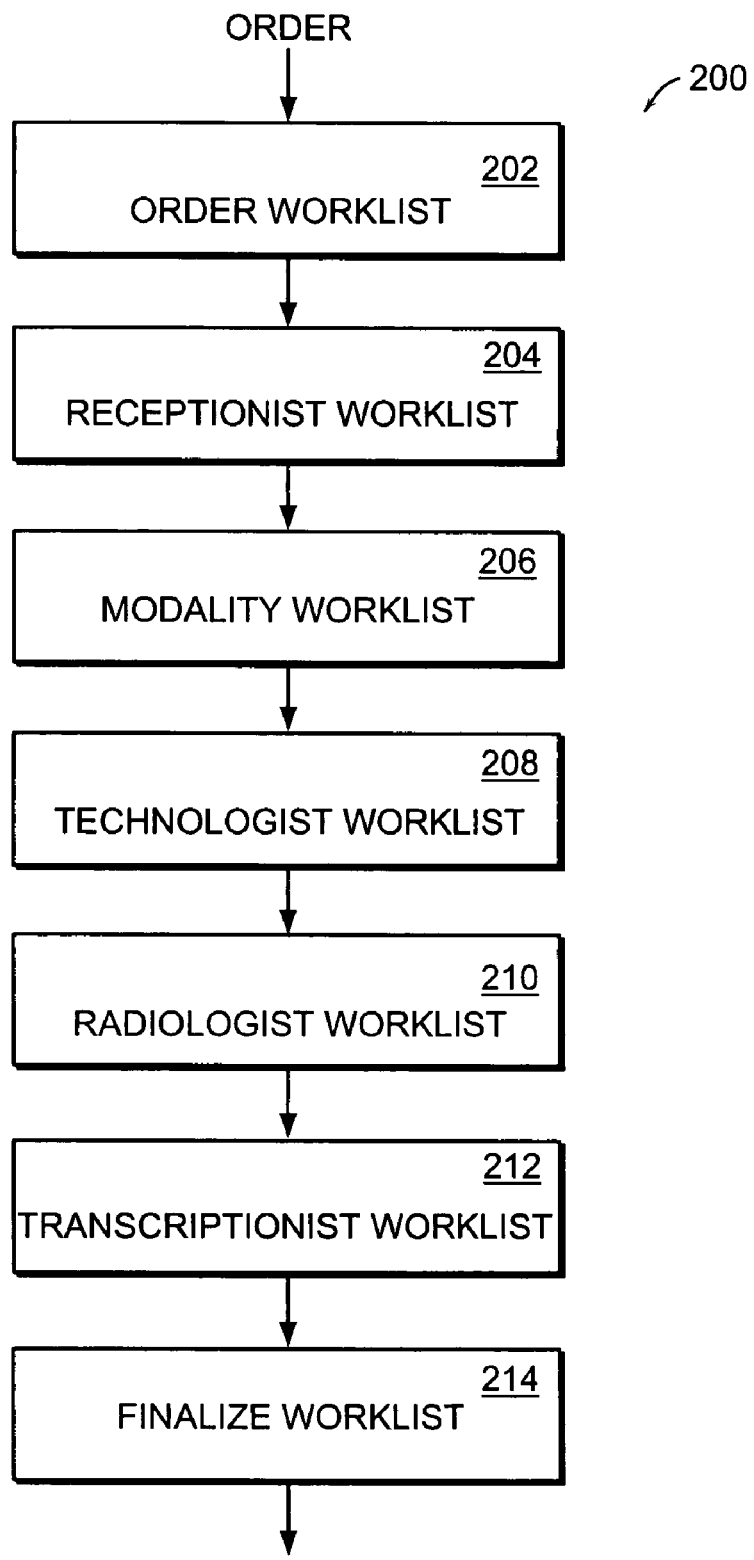
FIG. 2 is a block diagram showing the flow of an order through various worklists in an example usage scenario of a worklist system according to an embodiment of the invention.

FIG. 2 is a flow diagram depicting an exemplary usage scenario 200 of a worklist system according to an illustrative embodiment of the invention. This exemplary scenario involves ordering a study, including images, and tracking processing of the study through a final report being generated by a radiologist. It should be understood that the scenario of FIG. 2 represents only one possible way in which worklists may be used, and that the worklists described as part of this scenario are not the only worklists that may be in use in the system.

The same system that handles the worklists described below may display the same types of information, or even the same worklist items in numerous other worklists. For example, the worklist items displayed in a an individual radiologist's worklist may also be displayed in a radiology department worklist, or other worklists that are not part of the usage scenario described with reference to FIG. 2.

In the example use scenario 200 described with reference to FIG. 2, the process begins with a referring physician requesting that a patient study, such as an MRI be performed. In response to receiving this request, medical administrative staff, typically a clerk, enters an order for work to be performed. In some embodiments, the order may be entered in an order form that is displayed by the network server 114 on the workstation (typically a Web workstation, similar to the network workstations 116) of the clerk entering the order. The data entered by the clerk to submit an order preferably includes a variety of study-related information, such as the patient's name, medical ID number, date of birth, age, sex, the date and time that the procedure is to start, the modality and procedures or protocols to be observed in completing the study, a description of the study, information relating to the referring physician, and billing or insurance information. The information to be entered into an order is user configurable, and may be customized to fit the policies and procedures of hospitals or medical offices that use the worklist system.

In some illustrative embodiments, a search capability is provided within the order entry form (e.g., by a Java™ applet that requests data from the database 154), permitting the clerk who is entering the order to request information from the database 154 to fill out the required fields of the form. Additionally, the clerk is preferably able to edit or delete orders that have been entered. In some embodiments, the order entry form is completed by an automatic feed from a Hospital Information System (HIS) (not shown), Radiology Information System (RIS) (not shown), Electronic Medical Record System (EMR) (not shown), or other similar system. In other embodiments, the clerk is able to search the HIS, RIS, EMR or other similar system through a direct linkage to such systems available from the order entry form.

Once an order is entered or captured, information from the order is stored in the database 154, and the worklist module 108 prepares a worklist item, containing information from the order such as the patient's name, age, sex, patient ID, referring physician, and procedure to be performed. This worklist item is given a status of "ordered", and is made available for display in an order worklist 202 by the worklist module 108. The real-time worklist service 110 sends the new worklist item to any workstations that subscribe to the order worklist 202.

The order worklist 202 is typically viewed by medical administrative staff, such as clerks, who schedule procedures. A clerk may schedule an item in the order worklist 202, at which time the item's status is changes to "scheduled", and the worklist module 108 makes the item available in a receptionist worklist 204. The worklist module 108 may also make the item unavailable in the order worklist 202. The real time worklist service 110 sends messages to subscribers of the order worklist 202 and the receptionist worklist 204 that cause the item to be removed from displays of the order worklist 202, and added to displays of the receptionist worklist 204.

The receptionist worklist 204 is typically used by reception personnel, to check patients in for a procedure or study. When a patient checks in, the receptionist changes the status of the worklist item for that patient and procedure or study from "scheduled" to "arrived". Alternatively, the status can be changed to "cancelled" if the procedure is canceled. If the status is changed to "arrived", then the item may be removed from the receptionist worklist 204, and made available in an appropriate modality worklist 206.

For each medical imaging system (e.g., MRI systems, X-Ray systems, etc.), there may be a separate modality worklist. In some embodiments, a modality worklist exists for each individual system or department having a system. For example, if a hospital has an X-ray system associated with its ICU, and another X-ray system associated with its radiology department, each of these systems may have its own modality worklist.

Alternatively, modality worklists may be associated with wider groups, such as an entire department, all radiologists and technicians, etc. As will be described below, the worklists are configurable, as is the group of users who view a particular worklist. In many instances, it may be desirable to make worklist items available to a large set of users, to increase the opportunity for errors to be spotted.

The modality worklist 206 is typically viewed by a technician who handles orders for a particular modality. In some embodiments, information from items in the modality worklist may be transferred to a worklist or data handling mechanism associated with the modality. For example, MRI systems typically handle a list of jobs to be completed, and patient data associated with each such job within the MRI system. In cases where automatic transfer of this information is impractical or unavailable, the worklist items can be entered into the modality by a technician.

Once the images are properly scanned by the technician, the status of the worklist item is changed to "imaged". In some embodiments, this causes the worklist item to be made available in a technologist worklist 208, for verification. In some embodiments, the item remains in the appropriate modality worklist 208 to be verified. Some embodiments make items that have a status of "arrived" available in both the technologist worklist 208 and in an the appropriate modality worklist 206.

Once the status of a worklist item is "imaged", there may be one or more medical images associated with the worklist item. In some embodiments, the worklist item includes links to the images, and a user can view the images by selecting an action associated with the worklist item in his or her worklist display.

The technologist worklist 208 is a worklist used by a particular technician or technologist, or by a group of technicians or technologists to track images or studies that need to be verified. In some embodiments (i.e., those that make items with a status of "arrived" available in the technologist worklist 208), the technologist worklist 208 may also be used to determine which images need to be taken.

A technologist verifies the images and associated study information associated with an item in the technologist worklist 208, and then changes the status of the worklist item to "verified." The worklist item is then assigned to a radiologist, or to a group of radiologists. In some embodiments, this is done manually be the technologist, to help ensure that the correct radiologists receive the study. In some embodiments, the worklist module 108 automatically makes the item available in the worklists of appropriate radiologists or groups of radiologists, based on criteria associated with the worklists for those radiologists, as described below.

Radiologists may use a radiologist worklist 210 to view a list of studies that need to be read. When a radiologist reads a study in a worklist item from the radiologist worklist 210, he or she typically provides a dictated preliminary report associated with the study. In some embodiments, a voice or other media file containing the radiologist's dictation of the report may be stored by the system 100 (e.g., in database 154) and linked to the worklist item. In some embodiments, the dictation will be handled using more conventional equipment, such as a tape-based dictation machine. When a radiologist has finished reading a study, he or she may change the status of the study to "dictated", and make the worklist item associated with the study available on a transcriptionist worklist 212.

Transcriptionists take items from a transcriptionist worklist 212, and transcribe the dictated reports associated with those items into a preliminary report that is associated with the patient study data. When the preliminary report has been entered, the transcriptionist changes the status of the worklist item associated with the study to "preliminary report available", and makes the worklist item available to an appropriate radiologist to be finalized. In some embodiments, this may be done by making the worklist item available in a finalize worklist 214. In some embodiments, the worklist item will be made available in the radiologist worklist 210, but with a status of "preliminary report available", rather than "verified", so the radiologist will be able to immediately see that the worklist item needs to be reviewed and signed, rather than read.

Items in the finalize worklist 214 (or items with a status of "preliminary report available" in the radiologist worklist 210) may be reviewed by a radiologist. The radiologist may make any needed changes in the preliminary report, and then sign the report (digitally, in some embodiments), to finalize the report. Once the report is finalized, the status of the worklist item is changed to "final report available."

Once the status of a worklist item has been changed to "final report available," the report may be provided to the referring physician, and the worklist item may be made available to administrators to handle billing, insurance, and other administrative tasks.

The set of worklists and the use scenario described above provides one example of a set of worklists that may be managed in accordance with an embodiment of the invention. Although the worklists in this example are described as being somewhat narrow in function and in the classes of personnel to which they are available, this need not always be the case. For example, in some embodiments, the system may be configured to make all worklist items with particular attributes available in the radiologist worklist 210, rather than only those items with a status of "verified."

Additionally, there may be many other worklists that are used in a typical medical system that are not listed above. For example, there may be an emergency room worklist (not shown) that lists all of the worklist items for patients who are in the emergency room or who are en route to the emergency room, regardless of the status of the worklist items, so that the emergency room staff can immediately determine the status of any needed medical image information. Other examples of worklists that may be used in a typical medical system include referring physician worklists, hospital ward or department worklists, a master schedule worklist, film library worklists, worklists for preparing CDs containing patient studies, quality control worklists, and many others.

In preferred embodiments, there is considerable overlap between the worklists, to reduce errors by providing many opportunities for worklist items to be viewed. According to the illustrative embodiment, this is balanced with efficiency concerns, to provide each user a worklist containing items that are immediately relevant to that user, and that permit the user to quickly assess the tasks that must be performed. Since various users or groups of users may come to different conclusions regarding the balance between having extra information to reduce errors and having focussed information to enhance efficiency, the worklists are easily configurable, as described below. Generally, the worklists may be configured by a system administrator, on behalf of a hospital or institution, or by individual users.

Figure 3:
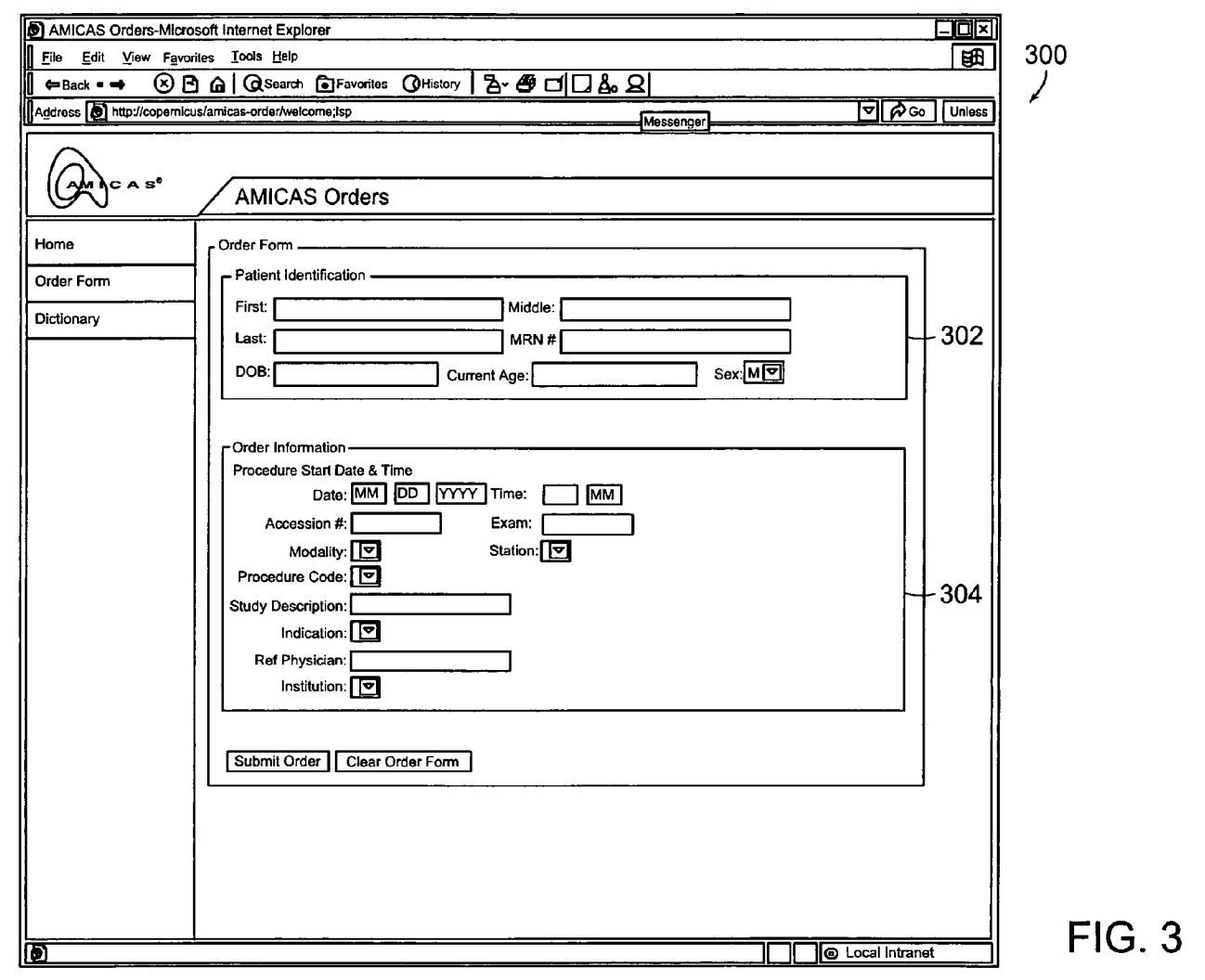

FIG. 3. shows an example of an order form that may be used to enter orders for images to be taken. An order form 300 may be displayed within a Web browser on a Web-based workstation, such as a network workstation 116. Alternatively, a similar order form can be used with specialized imaging workstations 118, or proprietary workstations.

As can be seen, the order form 300 includes a patient identification area 302 and an order information area 304. In the patient identification area 302, information identifying the patient is entered. This may include information such as a patient's name (first, middle, and last), a medical or insurance identification number, a birth date, age, and sex.

In the order information area 304, information relating to order may be entered. The information relating to the order may include the start date and time of a procedure, a modality identifier, a referring physician, information on the procedure to be performed, a study description, and other information concerning the study or procedure being ordered.

In operation, the order form 300 typically is sent to a workstation by the network server 114, for display within a Web browser. The information entered into the order form 300 is returned to the network server 114, using well known Web protocols, such as HTTP. The network server 114 will then provide the information from the order form 300 to the database module 112, which will store the information in the database 154 in an order or worklist item record. The information may then be retrieved and processed by the worklist module 108.

The order form 300 is just one way in which orders may be entered into a worklist system according to the invention. In some illustrative embodiments, orders may be entered using existing ordering and scheduling software, and the orders may be automatically transferred or imported into the worklist system.

In some embodiments, the layouts and fields shown in the order form 300 may be changed. Preferably, the layouts and fields shown in the order form 300 are easily reconfigurable by an administrator of a worklist system, and may be customized to meet the needs of the particular hospital or medical institution that is deploying a system according to an embodiment of the invention.

FIG. 4 shows an example of a worklist 400. The worklist 400 shown in FIG. 4 is an emergency room (ER) worklist, and shows entries in a variety of states in a workflow. Each such entry in the worklist 400 typically displays selected information on a worklist item or order.

As can be seen, the worklist 400 is organized according to date, showing items scheduled for each of three days, in date panels 401, 402, and 403. Arranging worklist entries according to date is only one option that may be employed by a user. In some embodiments, worklists may be arranged in panels according to date, patient, referring physician, procedure, position in workflow, or other criteria. Alternatively, in some embodiments, panels are not used, and all entries are listed within a single area of the worklist. Generally, worklists may be organized according to a basic organizing principle, such as the person viewing the worklist, the role of the person viewing the worklist, the location or geography associated with the worklist (e.g., an ER worklist, a radiology department worklist, a hospital floor or department worklist), time (e.g., check-in time, procedure time, time of last action, time of next action, etc.), modality, or other similar bases for organizing a worklist. More examples of the data around which a worklist may be organized is provided below with reference to FIG. 6.

Referring to FIG. 4, each entry in the worklist 400 includes numerous fields, including a patient name field 404, an age/sex field 405, a patient ID field 406, a time field 408, a referring physician field 410, a procedure field 412, a prior studies field 414, an images field 416, an alert field 418, and a workflow field 420.

The patient name field 404 shows the patient's name, typically with the last name appearing first. The age/sex field 405 shows the age and sex (M for male, F for female) of the patient. The patient ID field 406 shows an ID number for the patient. This ID number may be an internally assigned number, an insurance ID number, or any other unique ID number for the patient.

The time field 408 specifies the time at which the procedure is scheduled to be performed. The referring physician field 410 shows the name of the physician who referred the patient for the procedure, and the procedure field 412 specifies the procedure to be performed. The information in many of these fields corresponds to information entered in an order form, such as the order form 300. In some embodiments, selected fields, such as the patient name field 404, may be retrieved from a hospital or institutional database, based on the patient ID number in the patient ID field 406.

The prior studies field 414 shows whether there are any prior studies associated with this patient, and (through use of the small arrow located in this field) permits information on those prior studies to be displayed or hidden. For example, an entry 430 shows two prior studies in the prior studies field 414. The information on these prior studies is shown in entries 432 and 434. An entry 436 shows 1 prior study in the prior studies field 414, but this prior study is hidden.

The images field 416 shows how many images have been taken in this study. For example, the images field 416 of the entry 436 shows that five images have been taken. In some embodiments, these images may be linked to an entry in a worklist, and actions (in actions area 450, described below) may be selected to view the images.

The alert field 418 shows an alert status of the entry. This field may contain "STAT" in entries for patients that are in need of immediate attention.

The workflow field 420 shows the current status of an entry. Generally, the status will be similar to the possible status entries described above with reference to FIG. 2. For example, the entry 436 has a workflow field 420 that shows "Preliminary", indicating that a preliminary report has been entered. The entry 432 has a workflow field 420 that shows "Imaged", indicating that the entry has been imaged, but not yet verified.

In some entries, a temporary status may appear in the workflow field 420. A temporary status is generally used by the system to indicate that some temporary system activity is occurring, or that a user is in the process of updating the entry. For example, in the entry 430, the workflow field 420 shows a status of "Transferring". This is a temporary status, indicating that the system is in the process of transferring images from a modality into the image store 152. As another example of a temporary status, an entry may display "In Use" in the workflow field if, for example, a radiologist is currently in the process of reviewing images and dictating a preliminary report.

Entries in a worklist, such as the worklist 400, may be sorted based on a variety of the fields. For example, in some embodiments, a user may select to sort the worklist 400 based on the patient name field 404, the patient ID field 406, the time field 408, the referring physician field 410, the procedure field 412, the alert field 418, or the workflow field 420. Some embodiments may support sorting by any of the fields, and may permit specification of primary and secondary sort fields, where the secondary sort field is used to determine order when the values in the primary sort field are identical.

In some embodiments, entries in the worklist 400 may be hidden. For example, in the date panel 402, an entry states that five patients are hidden. The user may choose to display hidden entries, or may leave them hidden. Use of hidden entries permits the information displayed in the worklist 400 to be kept to a manageable amount, which can preferably be shown on a single screen. Advantageously, even when entries are hidden, critical information relating to the hidden entries, such as the amount and type of information that has been hidden, is visible in the worklist at all times. As a result, all clinicians who are using the worklist are immediately and continuously aware of the amount and type of information that has been hidden.

In some embodiments, the system may use various criteria, as described below, to determine which entries in a worklist should be hidden. In some embodiments, the user determines which entries should be hidden.

The left-hand portion of each of the entries in the worklist 400 displays an action area 450. The action area 450 contains icons that represent the various actions that may be performed on an entry in the worklist 400. For some entries, certain of the icons may be grayed out, indicating that the action represented by the grayed out icon is not available for that entry.

In FIG. 5, the action icons are shown more clearly for one of the entries in the worklist 400. In some embodiments, this larger view of the action icons may be displayed when a mouse pointer is left over the action area 450 for a period of time greater than a predetermined period of time, such as two seconds.

Selecting a "study" action icon 502 causes the system to display information (typically in a separate window) on the study associated with the worklist entry. This information typically includes the images associated with the study, permitting the user to view any images that are currently available for each entry in the worklist 400.

In response to a user selecting an "order" action icon 504, details of the order are displayed, typically in a separate window. In some embodiments, the user may be able to edit the order information from this display.

Selecting the "report" action icon 506 causes the system to display the report (if any) associated with the entry. In some embodiments, the "report" action icon 506 also permits the user to generate a report or edit a report. In some embodiments, this may be achieved by launching an external program to permit voice, multimedia, VR, or keyboard entry of the report.

The "burn CD" action icon 508 permits a user to write all of the online studies for a patient to a CD-ROM. This may be used to export information for a particular patient from the system for remote use, or to transfer patient records to another site. Preferably, the information recorded on the CD-ROM is stored in standard formats, such as JPEG 2000 for images, XML for data, or other standard formats, so that the information stored on the CD-ROM may be read or imported by a variety of software.

The "route" action icon 510 permits a user to manually route an entry to another worklist, or to route the study (including any associated images) to another system.

The "verify" action icon 512 permits a user to verify the images or other information associated with a study or worklist entry. Depending on the worklist, selecting the "verify" action icon 512 may cause the entry to be removed from the worklist display (this would not be the case for the ER worklist), and placed on one or more other worklist displays for reading the images associated with the study.

It should be understood that a real-time worklist according to an illustrative embodiment of the invention is based on several organizing principles, including the user interface. The ER worklist shown in FIGS. 4 and 5 illustrates a user interface according to an illustrative embodiment of the invention. Generally, the user interface for real-time worklists is organized consistently across all worklists, with patient and institution-related data organized in columns. Even when items in a worklist are hidden, critical details about the information are still visible in the worklist, so that clinicians are kept aware of the amount and type of information that is hidden. Additionally, as detailed in FIG. 5, the principal actions associated with a worklist are co-located for ease of use by clinicians. Additionally, further information may typically be accessed by clicking on fields contained in a worklist. For example, clicking on a patient's name may cause the system to display a worklist containing all of the studies related to that patient. Clicking on a modality may cause the system to display a worklist associated with that modality.

Another of the organizing principles of worklists is the data displayed in the worklist. FIG. 6. shows numerous types of data that may be included in the database 152, that may be used to organize worklists, and/or that may be displayed in a worklist item according to an illustrative embodiment of the invention. It should be understood that the list of types of data discussed here is not a fully inclusive list of all of the types of data that could be handled by a real-time worklist. In general, real-time worklists could be configured to handle most any kind of information that may be stored or displayed on tasks or workflow of any type.

A set of patient data 552 includes a variety of data related to the patient, such as the name age, or sex of the patient. The patient data 552 may also include medically relevant information on a patient, such as a diagnosis or prognosis. Additionally, administrative information on a patient, such as the patient's location within a hospital or medical institution, a patient ID, a medical record number, insurance information, or other administrative information may be included in the patient data 552. In addition to the information listed above, other information related to a patient may be included in the patient data 552.

A set of study data 554 includes a variety of information about a study, one or more of which may be associated with a patient. The study data 554 may include an accession number for the study, the number of images associated with the study the number of series associated with the study, the type of exam used for the study, the modality type, or other study-related information. It should be understood that the study data need not necessarily contain image data, and that some studies may include data related to lab results or other types of study data.

A set of institution data 556 includes a variety of information relating to the institution or location. This information may include the institution name, a location (such as a floor, department, etc.), the status or types of actions that have been scheduled and/or completed, a station ID within the institution, a treating physician, a referring physician, a modality, and other institution or location-related information.

A set of time data 558 includes various time-related information. The time data 558 may include, for example, the time scheduled for a specific relevant next action, the time of a last action, or other time-related information. Generally, time can include a year, week, day, hour, or minute, or other measures of time, depending upon the type of worklist and timespan that is relevant. Additionally, when displayed, time information can be absolute, or relative (e.g., how long from the current time).

A set of role data 560 includes information about the role or capacity in which the viewer of a worklist is acting. For example, the viewer of a worklist may be acting as a scheduler, reviewer, approver, etc., depending on the specific role of the individual at the time that they view a worklist. It should be noted that, for example, a single doctor may act in multiple roles, including the role of a private practitioner reviewing his or her patients only, an ER doctor interested in ER patients, a teaching doctor interested in patients being followed by attendings and interns, etc. There are also administrator, executive, and quality control roles, that may have access to more lengthy worklists or summary worklists, with an ability to access the data directly from activity logs kept by a real-time worklist system.

The patient data 552, study data 554, institution data 556, time data 558, and role data 560 may be used to organize worklists, and may be displayed in the columns in each worklist. This data can be broad-ranging, and provides a way of both identifying and accessing all types of clinically relevant data.

Another of the organizing principles of real-time worklists is the definition or scope of each worklist. The scoping rules of a worklist are used to select or filter the worklist items that are displayed, so that an individual using a worklist has a limited amount of information displayed at any given time. In preferred embodiments, the worklist items will be selected and filtered so that each user typically has no more than one screen of data to view at any given time. A worklist definition and scope should also permit a worklist to contain all of the information relevant for the person using the worklist to organize his or her activities. In preferred embodiments, the worklist definitions have scoping rules that are set up so there is substantial overlap between the worklists. This permits each set of data to be viewed by multiple clinicians, reducing the likelihood of errors.

Referring to FIG. 7, illustrative elements defining a worklist and worklist scoping rules are described. Worklists are defined by entries in a database, such as the database 154 or another data store, which determine which entries and fields will be available in the worklist, how the worklist will be organized, and what actions will be available. Each worklist can be associated with one or more users or groups of users. Worklists may be configured or created by an administrator or other personnel having the necessary permissions or access.

In general worklist definitions and scoping rules are configured by an institution, role, or individual, and can be structured so that one or more of the scoping rules associated with a worklist is primary, and can or cannot be overridden or ignored by an individual or role, depending upon the policies of the institution. Thus, an institution may define scoping rules that cannot be overridden, for example, by user preferences, or by a user worklist definition that inherits from or is based on an institution worklist definition.

A worklist record 600, which defines a worklist, includes a name field 602. In some embodiments, each worklist used in the system should have a unique name. The name field 602 may be used to specify a worklist when, for example, a worklist is associated with a user or group of users.

A check-in criteria field 604 is used to define scoping rules for the worklist by specifying the conditions under which the worklist module 108 will place an item in the worklist automatically when an order is entered or a worklist item is updated. In some embodiments, the check-in criteria field 604 includes numerous lists of items to be included or excluded. In the illustrative embodiment, these lists include a modality list, which lists the set of modalities for items to be included or excluded from the worklist. A device list may specify the set of specific devices (such as individual X-ray systems, CAT scan systems, or other medical imaging devices) for items to be included or excluded from the worklist.

A status list may specify the set of status indications for items that are to be included or excluded from a worklist. For example, if a technologist wants to see only items that have been imaged but not verified in his or her worklist, the "imaged" status can be specified as the only status for items to be shown in the worklist that will be used by that technologist.

A study description list may provide a list of words or patterns which, if present in the study description field of an order or worklist item, will cause that order or worklist item to be included or excluded from the worklist. The list of words or patterns may include wildcards, such as "*", which will match any combination of zero or more characters. In some illustrative embodiments, such wildcards are used in many of the lists.

A reading physician list may specify a set of reading physicians against which items will be checked, and included or excluded from the worklist based on whether the reading physician matched one of the reading physicians in the list. Similarly, a referring physician list may be used to include or exclude orders or worklist items from particular referring physicians.

The check-in criteria field 602 may also include a flag that indicates that only urgent (e.g., "STAT") orders or worklist items are to be automatically placed in the worklist.

A relative time indicator may also be included in the criteria field 602. Such an indicator causes only orders scheduled within a specified time window to be included in the worklist. This time window may be specified by either absolute or relative time. For example, an absolute time window might specify "all procedures scheduled between 3:00 PM and 4:00 PM should be included," while a relative time window might specify conditions such as "all procedures scheduled within the next hour should be included.".

According to the illustrative embodiment, when the check-in criteria field 602 includes entries in more than one of these lists, the check-in criteria for the worklist is considered as being the AND of all the criteria in the various lists. Also, if the check-in criteria field 602 is left empty, then no items will be automatically checked into the worklist, and only orders or items that are manually placed in the worklist will be included in the worklist.

A hide criteria field 604 specifies rules, in the form of the lists of conditions, for determining whether an order or worklist item should be "hidden" by default. The hide criteria field 604 may have lists similar to those in the check-in criteria field 602, to specify which items should be hidden by default. In some embodiments, only a status list, specifying a set of status values that should cause an item to be hidden (or not hidden) is specified in the hide criteria field 604.

If the hide criteria field 604 is empty, then no orders or worklist items will be hidden by default. Generally, users should be able to manually hide items in the worklist regardless of the contents of the hide criteria field 604 (unless this conflicts with institutional policy).

A checkout criteria field 606 specifies further scoping rules for the worklist by defining conditions under which the worklist module 108 will automatically remove items from the worklist. The checkout criteria field 606 may have lists similar to those in the check-in criteria field. In some embodiments only a status list, specifying a list of status entries that should cause an item to be removed (or not removed), and a time indicator, indicating that items older than a specified amount of time should be removed may be placed in the checkout criteria field 606.

If the checkout criteria field 606 is empty, then items will not be automatically removed from the worklist. In some embodiments, items that have been manually added to the worklist will not be automatically removed, regardless of the conditions specified in the checkout criteria field 606.

A display field 608 specifies rules for displaying worklist items in a worklist. In an illustrative embodiment, the display field 608 specifies the set of attributes of an order or worklist item that are to be displayed in entries in the worklist. For example, in the worklist 400 of FIG. 4, the displayed attributes include patient name, age, sex, patient ID, time, referring physician, procedure, prior studies, images, alert, and workflow. The display field 608 also permits the order in which these attributes will be displayed to be specified.

Additionally, the display field 608 may be used to specify if any attribute (such as date, patient, procedure, etc.) will be used to define multiple separate panels in the worklist, similar to the date panels 401, 402, and 403 shown in FIG. 4. The display field 608 also includes information on which fields in a worklist will be used by default to sort the worklist.

Actions field 610 contains a list of the action items that users of the work list will be able to access. In some embodiments, the actions that may be specified in the actions field 610 include a view report action, a generate report action, a view order action, a view tech notes (i.e., notes entered by a technician or technologist) action, a study completion action, a launch external viewer action, a CD burning action, and a routing action. Certain of these actions may use additional parameters. For example, the launch external viewer action may include information on the external viewer to be launched.

While the worklist record 600 may permit a high degree of customization, in many cases little or no customization will be needed. In accordance with some embodiments of the invention, multiple different types of users should preferably see the same information in their worklists, to reduce the occurrence of errors by submitting each worklist item to a high degree of scrutiny. Additionally, although worklists could be highly customized, to show only information that is clearly relevant to the person viewing the worklist, the extra information may help provide context for the more relevant information, which may be useful in understanding the information, and in reducing errors.

Advantageously, with wide deployment of worklists, the system may become effectively self-managing, as each user, role, group of users, etc. sets up their individual worklists to display the information that is relevant to them, a certain degree of overlap will occur. This overlap, combined with the real-time, unprompted updating of all worklists, in accordance with the invention, can greatly reduce the occurrence of errors.

Figure 8:
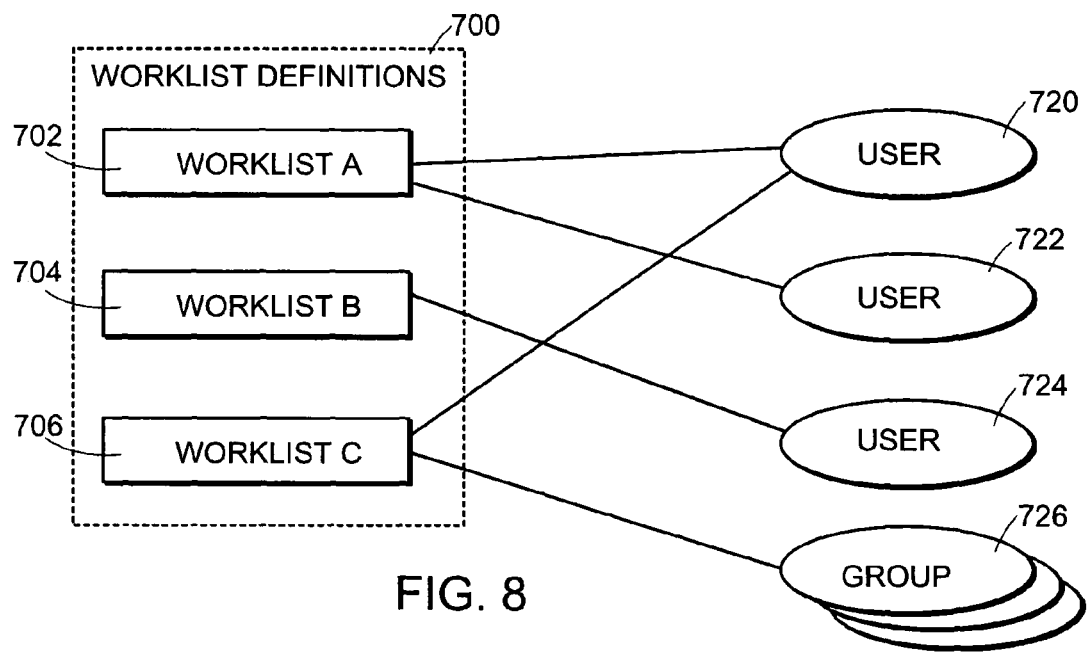
FIG. 8 is a block diagram showing the association of worklists with particular users or groups, in accordance with an embodiment of the invention.

Once a worklist is defined using these fields, it may be associated with users or groups of users. FIG. 8 shows a block diagram demonstrating such associations. As can be seen, a set of worklist definitions 702 includes a worklist A 704, a worklist B 706, and a worklist C, 708. The worklist A 704 is associated with a user 720 and a user 722. This means that each of the users 720 and 722 may view the worklist A 704. Similarly, the worklist B 706 is associated with a user 724, and the worklist C 708 is associated with a group 726 (which may contain numerous users), and the user 720.

In some embodiments, each association between a worklist and a user or group has user/group preferences. For example, the association between the worklist A 704 and the user 720 has may include preferences specifying how the user 720 wishes to view the information in the worklist A 704. Similarly, the association between the worklist C 708 and the group 726 may include preferences that determine how members of the group 726 view the information in the worklist B 708. In some embodiments, there may be a separate set of preferences for each user in a group.

Generally, the preferences include information about how a particular user or group wishes to view a worklist. In some embodiments, this information may include the user's preferred sort orders, the user's preferred fields or attributes to view in each entry, and the number of entries that may be displayed in a single page of the user's display. In some embodiments, these preferences may override display information in the display field 608 of a worklist definition.

Figure 9B:
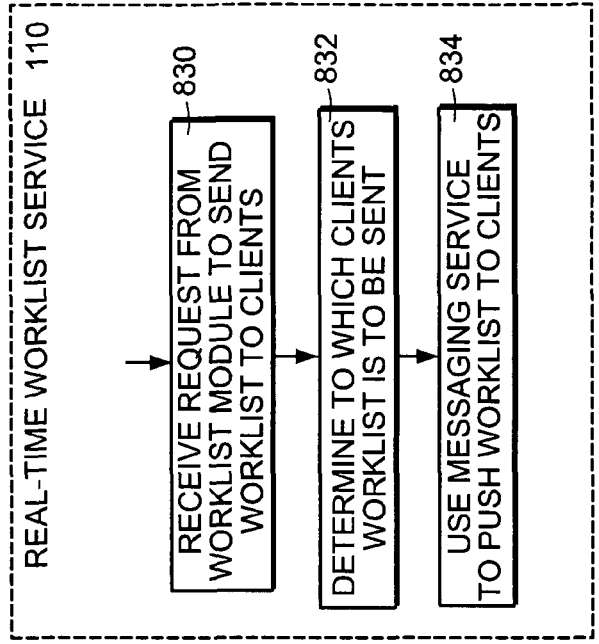
FIGS. 9A-9C are flowcharts showing the operation of a procedure for processing worklists used in a worklist module, a real-time worklist service, and a worklist client, according to an embodiment of the invention.
Figure 9C:
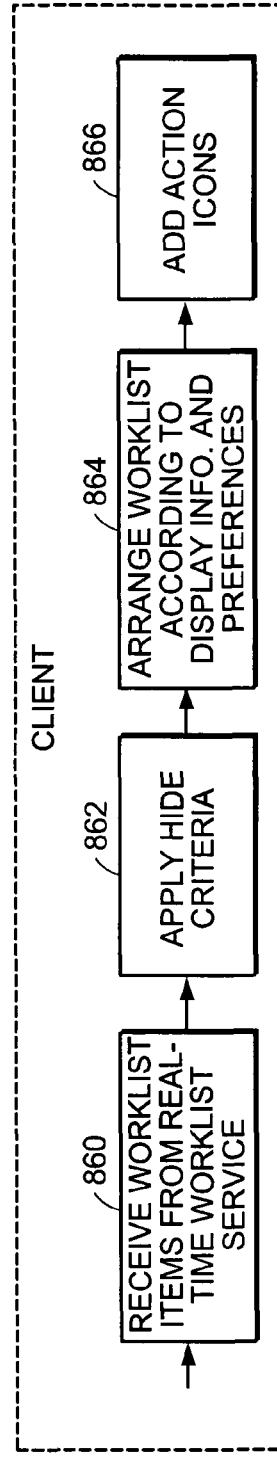
Figure 9A:
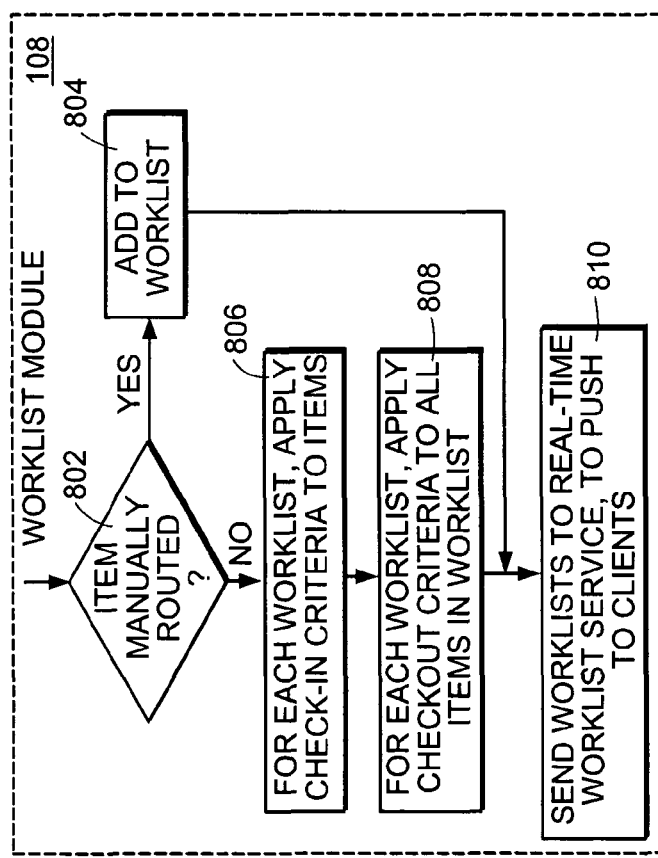

FIG. 9A depicts a flowchart of an illustrative procedure used in an embodiment of worklist module 108 for updating worklists. This procedure is triggered by events that may change the state of worklist items. These events include, for example, entry of a new order, editing an order, canceling an order, updating patient data, receiving images (either imported or from a modality), deleting a study, viewing a study, scheduling a procedure, checking in a patient, verifying images, dictating a report, transcribing a preliminary report, signing a report, or any other action that may change the state of worklist items.

In step 802, the worklist module 108 determines whether the action is the manual routing of an item to a worklist. If so, then in step 804, the item is added to the worklist to which it was routed. Manually routed items are generally not subject to filtering by the check-in criteria or other criteria for including or excluding an item from a worklist.

In step 806, if the action was not manual routing of an item, then for each worklist, the worklist module 108 determines whether the item or items, as modified by the action that triggered the procedure, should be included or excluded from the worklist. This is done by applying the criteria in the check-in criteria field 602 of the worklist definition to all items that may have been affected by the triggering action. Items that the check-in criteria indicate should be in the worklist are added (if not already present in the worklist), or updated (if already present in the worklist).

In some embodiments, the worklist module 108 applies the various criteria to all worklist items periodically. In some embodiments, any action that triggers the procedure causes all worklist items to be checked against all worklists (i.e., any action can cause a rebuilding of all worklists). Since the number of worklist items will generally be relatively small—typically not more than tens of thousands, and the number of worklists will generally be small, typically not more than a few hundred, applying all criteria from all worklists to all worklist items, to completely rebuild all the worklists is a task that can be carried out very quickly by modern computing equipment.

Next, in step 808, for each worklist, the checkout criteria in the checkout criteria field 606 of the worklist are applied to the items in the worklist. Any items that the checkout criteria indicate should be removed are removed. In step 810, the worklists are sent to the real-time worklist service 110, where they will be pushed to appropriate clients.

FIG. 9B is a flowchart depicting an exemplary procedure carried out by the real-time worklist service 110 to push the worklists to the clients according to an illustrative embodiment of the invention. First, in step 830, the real-time worklist service receives a request from the worklist module 108 to send a worklist to clients.

In step 832, the real-time worklist service 110 determines to which users the worklist should be sent. In some embodiments, this may be achieved by examining the associations between worklists and users or groups. If a user or group subscribes to a worklist, then the worklist should be pushed to clients that display worklists to that user, or to users in the group.

In step 834, the real-time worklist service 110 pushes the work to the appropriate clients. In some embodiments, this is accomplished using a messaging service, such as a Java™ Message Service (JMS) implementation. Suitable JMS implementations are available from numerous sources, including Sun Microsystems, of Santa Clara, Calif., International Business Machines Corporation, of Armonk, N.Y., or from JBOSS.ORG.

Advantageously, by pushing the information to clients, the clients are able to receive updates almost as soon as an event occurs that causes the worklists to be updated. This rapid updating of the worklists helps reduce errors by ensuring that the worklists are displaying current information, and that all users see a consistent view of the state of the worklist items.

In some embodiments, the worklist information that is sent to the client is transferred in a standard format, such as XML. Using such a standard format for the worklist data permits clients to be built to read the data, without requiring that the clients be able to read a proprietary message format.

FIG. 9C shows a flowchart depicting an exemplary procedure carried out by a client to display a worklist that is received from the real-time worklist service 110 according to an illustrative embodiment of the invention. The client may be a network workstation 116, an imaging workstation 118, or any other device that is capable of receiving messages sent by the real-time worklist service 110, such as a workstation, a personal digital assistant, or a wireless device.

In step 860, the client receives a message from the real-time worklist service 110 containing one or more worklist items. As discussed above, in some embodiments, the worklist items may be in XML format, and should be parsed.

Next, in step 862, the client applies the hide criteria from the hide criteria field 604 of the worklist, to determine which items in the worklist should be automatically hidden. In some embodiments, the client may receive a worklist definition, including the hide criteria field, when the client subscribes to a particular worklist, or as a part of a message from the real-time worklist service 110 when a worklist is sent to the client.

In step 864, the display information from the display field 608 is used to determine which information to display in worklist entries, and how to display it. The client arranges and sorts information from the received worklist items into displayed entries according to the information in the display field 608 of the worklist. In some embodiments, user preferences may be used to override portions of the display information to determine the arrangement and sorting of entries in the work list.

In some embodiments, the preferences may be stored on the client. In some embodiments, the preferences may be sent to the client when a user logs onto the system, or when the worklist information is sent to the client.

In step 866, the client adds action icons to worklist entries to represent the actions in action field 61 0. Certain of the actions may be unavailable for particular worklist entries. These unavailable actions are grayed out.

FIGS. 10A-C show further examples of worklists according to an illustrative embodiment of the invention. FIG. 10A shows an additional example of an ER worklist 902. As can be seen, the ER worklist 902 includes numerous worklist items, each containing data including patient data (such as name, age, sex, and patient ID), study data (such as modality, procedure, priors and images), and institutional data (such as referring physician, alert, and workflow status). The worklist is organized by date, and includes hidden items, with descriptions of the number and type of the hidden items.

In FIG. 10B, a radiologist worklist 920 is shown. It should be noted that the radiologist worklist 920 includes the same data as was present in the ER worklist 902, and contains many of the same entries as the ER worklist 902. This overlap means that both the radiologists who view the radiologist worklist 920 and the ER personnel who view the ER worklist 902 see many of the same worklist items, with the same data, increasing the probability that any errors will be spotted and acted upon.

FIG. 10C shows a referring physician worklist 940, which lists only the patients that are of interest to particular referring physicians. As can be seen, much of the data is the same as is shown in the ER worklist 902 and the radiologist worklist 920, but the worklist 940 does not include information on images, and includes time information relating to the last action on each patient. Additionally, the referring physician worklist 940 is not organized by date, but is sorted according to the referring physician. Nonetheless, the worklist items list similar data in a manner that is reasonably consistent with the way in which the worklist items in the ER worklist 902 and the radiologist worklist 920 are displayed. Additionally, there are several worklist items that overlap with the ER worklist 902 and the radiologist worklist 920.

Having overlapping data that is updated in all of these worklists in nearly real-time as changes occur in the data, and displaying the data in a consistent manner across the worklists provides a useful combination of features for reducing the occurrence of errors. Because of the overlap in both worklist items and the data displayed for each worklist item in the worklists, the data will be scrutinized by numerous clinicians, with numerous different role, thereby increasing the likelihood that errors will be spotted and acted upon. The real-time, unprompted updates to the worklists help to ensure that the data in each worklist is always current, further reducing the occurrence of errors.

In some embodiments, the functionality of the systems and methods described above may be implemented as software on a general purpose computer. In such an embodiment, the program may be written in any one of a number of high-level languages, such as FORTRAN, PASCAL, C, C++, LISP, JAVA, or BASIC. Further, the program may be written in a script, macro, or functionality embedded in commercially available software, such as EXCEL or VISUAL BASIC. Additionally, the software could be implemented in an assembly language directed to a microprocessor resident on a computer. For example, the software could be implemented in Intel 80×86 assembly language if it were configured to run on an IBM PC or PC clone. The software may be embedded on an article of manufacture including, but not limited to, a "computer-readable medium" such as a floppy disk, a hard disk, an optical disk, a magnetic tape, a PROM, an EPROM, or CD-ROM.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

What is claimed is:

1. A method of providing worklist information in substantially real-time to users of a medical data management system, the method comprising:
   a) receiving a plurality of requests at a network server for patient studies to be performed,
   b) receiving at said network server, information associated with each requested patient study to be performed, the patient study information including at least: a patient ID, a referring physician, a start time and start date of a patient study to be performed, and a procedure type;
   c) storing the associated patient study information for each requested patient study in a data store coupled to the network server as a worklist item record;
   d) preparing by a patient procedure worklist module, a plurality of worklist items wherein each worklist item corresponds to one of the requested patient studies requested at said network server, wherein each of the prepared plurality of worklist items includes a set of data items comprising: (1) the associated patient study information received at said step (b), and (2) a workflow status indicator, and optionally (3) pointers to medical image data in an image store; wherein a plurality of workflow status indicators indicate the status of a worklist item included in a patient study worklist for a patient related activity to be performed or that has been performed on behalf of the patient, wherein said status indicators comprise indicia including at least one of: patient study ordered, patient study scheduled, patient study arrived, patient study cancelled, patient study imaged, patient study verified and patient study completed; and wherein the associated patient study information is selected for display on subscribing client computers based on a customizable set of display attributes;
   e) assembling by the patient procedure worklist module, at least two real-time worklists from the plurality of worklist items by employing a customizable set of scoping rules which include criteria to determine which worklist items are included in the at least two real-time worklists and to provide substantial overlapping information between worklists;
   f) providing the at least two real-time worklists to respective subscribing clients for display on subscribing client computers in substantially real-time, by pushing from a web-based real-time worklist service module at the network server, the at least two real-time worklists, in accordance with the HTTP(S) protocol, for display on said subscribing client computers,
   g) updating the at least two real-time worklists as events occur which change the state of at least one worklist item included within said at least two real-time worklists; and
   h) pushing the updated at least two real-time worklists, via the HTTP(S) protocol, to the subscribing clients for display on the subscribing client computers, in substantially real-time, in response to said change of state of at least one worklist item.

2. The method of claim 1, wherein the customizable set of rules is client customizable.

3. The method of claim 1, wherein the customizable set of rules is customizable by a system administrator.

4. The method of claim 1, wherein the set of data items includes medical study data.

5. The method of claim 1, wherein the set of data items includes patient data.

6. The method of claim 1, wherein the set of data items includes patient location information.

7. The method of claim 1, wherein the set of data items includes institution data.

8. The method of claim 1 comprising automatedly generating a subset of the plurality of worklist items for inclusion in a worklist.

9. The method of claim 1 comprising automatedly updating a subset of the plurality of worklist items in real-time in response to an action being taken with respect to the set of data items.

10. The method of claim 1 comprising automatedly removing from at least one of the one or more worklists a subset of the worklist items previously assembled into the at least one of the one or more worklists in response to an action being taken with respect to the set of data items.

11. The method of claim 1 comprising automatedly adding one or more of the worklist items not initially assembled into at least one of the one or more worklists in response to an action being taken with respect to the set of data items.

12. The method of claim 1 comprising providing a graphical user interface to enable a user to enter a subset of the plurality of worklist items.

13. The method of claim 1, wherein assembling the one or more worklists comprises receiving orders for medical studies.

14. The method of claim 1, wherein assembling the one or more worklists comprises determining which of the plurality of worklist items are assembled into each of the one or more worklists based at least in part on a set of check-in criteria.

15. The method of claim 14, wherein the check-in criteria includes a specification of one or more modalities associated with each particular medical study.

16. The method of claim 14, wherein: each of the plurality of worklist items includes a scheduled time: the check-in criteria includes a time window for each of the one or more worklists; and each of the one or more worklists includes those of the plurality of worklist items having a scheduled time that falls within its time window.

17. The method of claim 14, wherein: each of the plurality of worklist items has an associated data value in the set of data items; the check-in criteria includes one or more data values for each of the one or more worklists; and each of the one or more worklists includes those of the plurality of worklist items having a data value that matches the one or more data values in the check-in criteria for that worklist.

18. The method of claim 14, wherein: each of the plurality of worklist items includes an associated status; the check-in criteria includes one or more status values associated with each of the one or more worklists; and each particular one of the one or more worklists includes ones of the plurality of worklist items that have an associated status value that matches an associated status value for the particular one of the plurality of worklists 19. The method of claim 1, wherein pushing the one or more worklists to the one or more client computers for display comprises using a messaging system to send the one or more worklists to the one or more client computers.

20. The method of claim 19, comprising employing a standards based messaging system.

21. The method of claim 1, wherein assembling the one or more worklists comprises applying a set of checkout criteria, which at least in part determine which ones of the worklist items included in a worklist should be removed from the worklist.

22. The method of claim 1, wherein each of the one or more worklists is associated with one or more users, and wherein pushing the one or more worklists to one or more client computer comprises determining which client computers should receive the worklist based at least in part on the users with which the worklist is associated.

23. The method of claim 1, wherein the medical data management system manages a medical imaging system, and wherein the set of data items includes a pointer to a medical image.

* * * * *